United States Patent [19]
McSoley

[11] Patent Number: 5,797,390
[45] Date of Patent: Aug. 25, 1998

[54] NASAL INHALER HAVING A DIRECTED SPRAY PATTERN

[76] Inventor: Thomas E. McSoley, 6477 N. Chester, Indianapolis, Ind. 46220

[21] Appl. No.: 611,727

[22] Filed: Mar. 6, 1996

[51] Int. Cl.⁶ ................................................. A61M 11/00
[52] U.S. Cl. ......................... 128/200.23; 128/200.14
[58] Field of Search .................. 128/200.23, 203.18, 128/203.12, 203.15, 203.23, 207.18, 200.14; D24/110

[56] References Cited

U.S. PATENT DOCUMENTS

| | | | |
|---|---|---|---|
| 690,527 | 1/1902 | Moores | 604/94 |
| 1,638,532 | 8/1927 | Kallmeyer | 604/279 |
| 2,445,653 | 7/1948 | White | 128/200.14 |
| 2,582,529 | 1/1952 | Curry et al. | 128/200.22 |
| 2,906,265 | 9/1959 | Samuels | 128/200.23 |
| 4,771,769 | 9/1988 | Hegemann et al. | 128/200.22 |
| 5,116,311 | 5/1992 | Lofstedt | 604/54 |
| 5,331,954 | 7/1994 | Rex et al. | 128/200.22 |

Primary Examiner—Mickey Yu
Assistant Examiner—William J. Deane, Jr.
Attorney, Agent, or Firm—Woodard, Emhardt, Naughton Moriarty & McNett

[57] ABSTRACT

A nasal inhaler having a directed spray pattern. The nasal inhaler includes an attachment which is sized and shaped to fit within a nostril. A medication spray emitted by the inhaler (such as by use of a propellant or from mechanically squeezing the inhaler) is directed to a lateral sidewall of the nose by the attachment. The attachment also prevents contact of the medication with the nasal septum or the back of the nasal cavity.

16 Claims, 2 Drawing Sheets

NASAL INHALER HAVING A DIRECTED SPRAY PATTERN

TECHNICAL FIELD OF THE INVENTION

The present invention generally relates to nasal inhalers and, more particularly, to a nasal inhaler having a directed spray pattern.

BACKGROUND OF THE INVENTION

The nose has become an important route for the delivery of medication by absorption in a number of medical fields. Nasal sprays and inhalers have been widely used to locally treat upper respiratory tract infection, sinusitis, allergic conditions, and reactive airway disease. More recently, the nasal mucosa has also become a preferred route of administration of many other drugs, such as pain medications, hormones, and (in the near future) insulin. This route of medication administration has many advantages over oral, intramuscular and intravenous administration.

However, there are disadvantages to the delivery of medication by nasal absorption. These include local irritation, bleeding, infection, and variable absorption. Most of the disadvantages occur when the medication, the carriers, and/or the propellant comes into contact with the nasal septum. The septum is a cartilage and bone structure that divides the nose into two halves. It is covered with a thin mucous membrane having a limited blood supply, and is easily irritated by contact with medications and propellants. The lateral wall of the nose, in contrast, has a rich blood vessel plexus which is only rarely irritated by these medications and propellants.

Prior art nasal inhalers are based directly upon the designs of lung inhalers. Lung inhalers work best with an even and random distribution of medication and propellants, and consequently this is what is produced by the prior art nasal inhalers. Such inhalers therefore deliver medication and propellants straight up the nasal cavity. A portion of the medication and propellants are delivered to the back of the nose and into the stomach, thereby wasting the medication and possibly irritating the stomach, while another portion is delivered to the nasal septum, possibly producing irritation, ulceration, perforation of the septum, and increased risk of infection.

Nasal inhalers would be more effective and less irritating if the medication was directed toward the lateral sidewall of the nose where the mucosa is thicker and the blood supply richer. This is also the area where sinusitis infections and allergic reactions occur in the nose, therefore it is desirable to apply treatment medications directly to this area. There is therefore a need in the prior art for a nasal inhaler which directs the medication and propellant stream to the lateral sidewall of the nose and prevents contact with other portions of the nose, particularly the septum. The present invention is directed toward meeting this need.

SUMMARY OF THE INVENTION

The present invention relates to a nasal inhaler having a directed spray pattern. The nasal inhaler includes an attachment which is sized and shaped to fit within a nostril. A medication spray emitted by the inhaler (such as by use of a propellant or from mechanically squeezing the inhaler) is directed to a lateral sidewall of the nose by the attachment. The attachment also prevents contact of the medication with the nasal septum or the back of the nasal cavity.

In one form of the invention a nasal inhaler having a directed spray pattern is disclosed, comprising a container adapted to hold a quantity of medication and including a container outlet; wherein the container is operable to emit a spray of the medication from the container outlet when activated; and lateral sidewall of a nose when the container outlet is inserted into the nose prior to activation.

In another form of the invention an attachment for connection to a spray outlet of a nasal medication container is disclosed, the attachment comprising a body member sized and shaped to fit into the nose; an opening formed in the body member such that the opening is adjacent a lateral side wall of the nose when the attachment is inserted into the nose; and a passage formed in the body member, the passage coupling the spray outlet to the opening; wherein the nasal medication container is operable to emit a spray of the medication from the spray outlet when activated; and wherein the attachment is operable to direct the spray to the lateral sidewall when the body member is inserted into the nose.

DESCRIPTION OF THE PREFERRED EMBODIMENT

Figure 1:
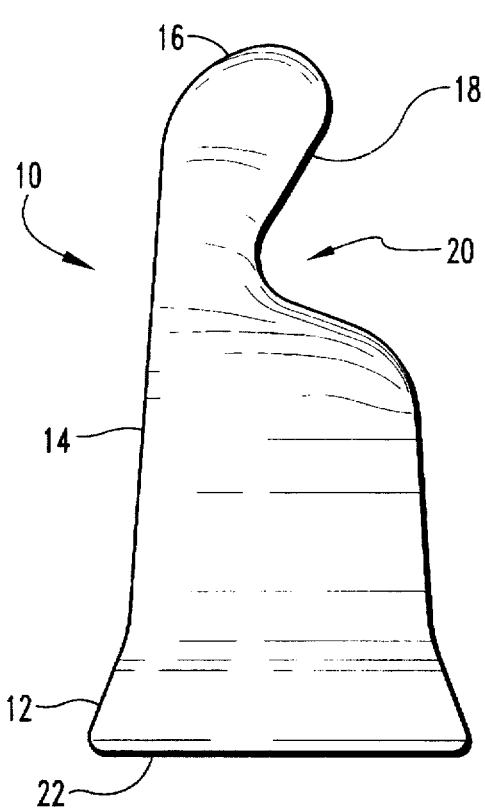
FIG. 1 is a side elevational view of a first embodiment nasal inhaler of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
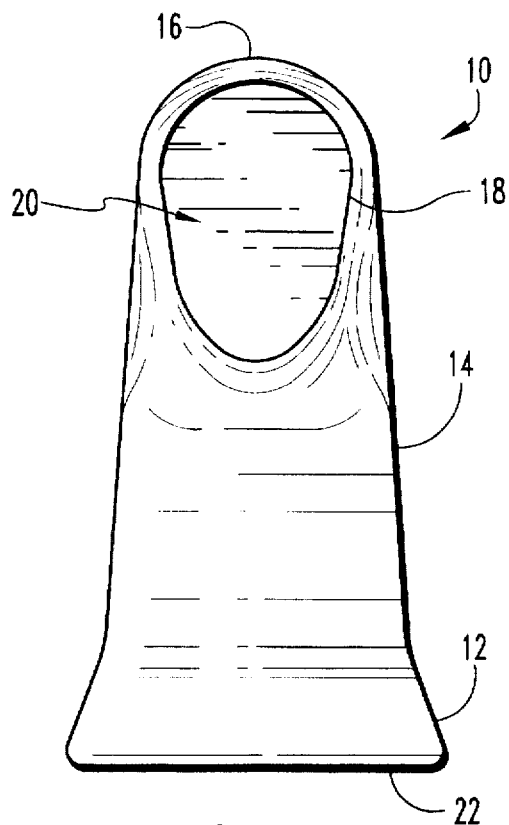
FIG. 2 is a front view of the first embodiment nasal inhaler of the present invention.
Figure 3:
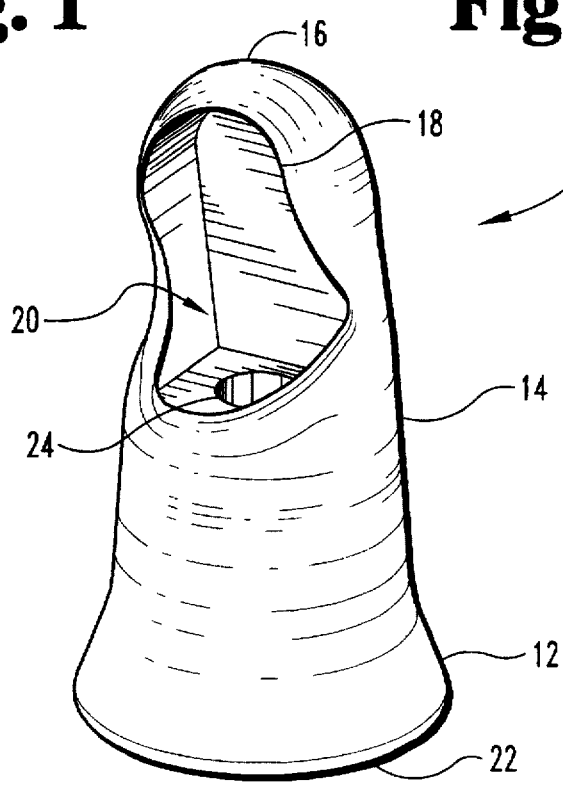
FIG. 3 is a perspective view of the first embodiment nasal inhaler of the present invention.

Because of the tendency for medications, carriers and propellants to irritate the nasal septum, it is common practice for doctors to instruct their patients to insert the outlet of the nasal inhaler or atomizer into the nostril and point the outlet toward the lateral sidewall of the nose prior to administering the medication. While this procedure is better than administering the medication straight into the nasal cavity, compliance with this procedure by the patient is rather low. Additionally, even though the medication is directed toward the lateral wall of the nasal cavity, it is not prevented from rebounding from the lateral wall and landing upon the nasal septum or being delivered to the back of the nose and into the stomach. In order to solve the problems involved with the delivery of medication by prior art nasal inhalers and atomizers, a nasal inhaler output attachment is provided by the present invention, as illustrated in FIGS. 1–3 and indicated generally at 10. The attachment 10 is generally sized and shaped so as to fit snugly within the nostril (human or animal). The proximal end 12 of the attachment 10 is preferably formed in an outward flair in order to discourage the user from inserting the attachment 10 too far into the nasal cavity. The attachment 10 further includes a generally frustoconical body portion 14 and a rounded distal end 16. The longitudinal distance from the flaired proximal end 12 to the rounded distal end 16 is approximately the length of the patient's nostril.

The attachment 10 further includes an opening 18 formed in the body portion 14 which extends from approximately the midpoint of the attachment 10 and into the rounded distal end 16, thereby forming a hooded cavity 20 therein. A longitudinal axial bore or passage is formed from a proximal end 22 of the attachment to an opening 24 into the hooded cavity 20.

Figure 6:
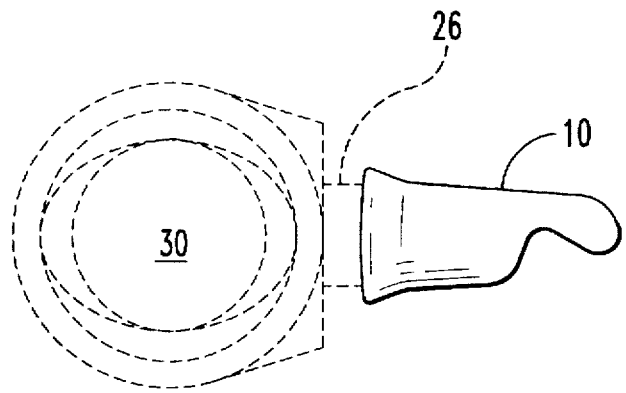
FIG. 6 is a top plan view of the first embodiment nasal inhaler of the present invention affixed to a medication dispensing apparatus.
Figure 5:
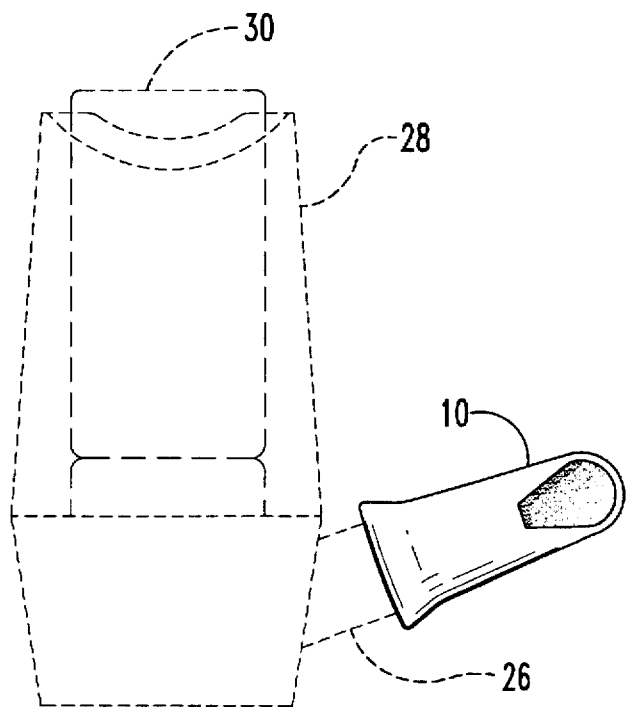
FIG. 5 is a side elevational view of the first embodiment nasal inhaler of the present invention affixed to a medication dispensing apparatus.
Figure 4:
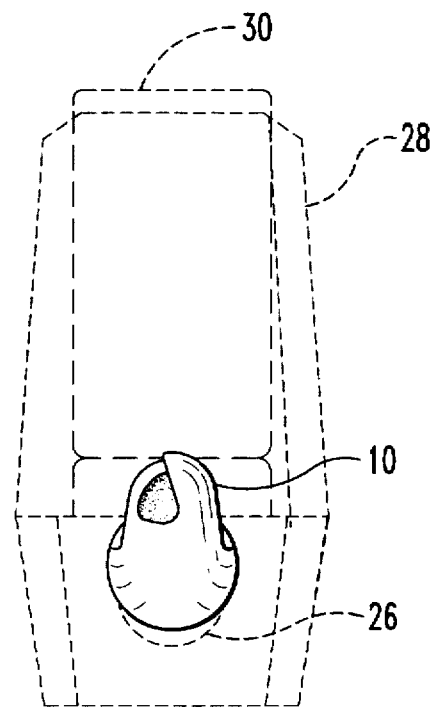
FIG. 4 is a front elevational view of the first embodiment nasal inhaler of the present invention affixed to a medication dispensing apparatus.

As illustrated in FIGS. 4–6, the nasal inhaler output attachment 10 may be attached to the output tube 26 of a standard nasal inhaler 28. Such attachment may be permanent or removable. The nasal inhaler 28 includes a canister 30 of medication and propellant which is fitted therein. When the canister 30 is depressed down into the inhaler 28, a spray of medication is delivered out of the output tube 26. With the attachment 10 in place on the output tube 26, this stream of medication is directed through the opening 24 and into the hooded cavity 20. The attachment 10 may be used equally effectively with a nasal inhaler in the form of a squeeze bottle, wherein medication is delivered from the output tube by squeezing the bottle, as is known in the art.

In use, the patient inserts the attachment 10 into the nostril such that the hooded cavity 20 is facing the lateral side wall of the nasal cavity. When fully inserted, the rounded end 16 seals off the back of the nasal passage, while the edges 18 of the hooded cavity 20 contact the lateral side walls of the nose. Once in this position, the canister 30 may be depressed into the nasal inhaler 28, thereby releasing a spray of medication which enters the hooded cavity 20. Because the hooded cavity 20 is only open to the lateral side walls of the nose, medication may only be applied to this surface. Furthermore, the closed rounded end 16 prevents delivery of the medication from the back of the nose and into the stomach. Also, the septum of the nose is completely covered by the body 14 of the attachment 10. There can therefore be no communication between the medication and the nasal septum. In order to apply medication to the opposite nostril, the attachment 10 is simply rotated 180° on the output tube 26 and the same procedure is followed with the other nostril.

It will be appreciated that the present invention represents an advance over the prior art in that the dispensed medication is directed specifically to the lateral side wall of the nose and is further prevented from contacting either the nasal septum or the rear of the nasal cavity. Such directing of the medication spray pattern is useful for all types of medication which are delivered via nasal inhalers. For example, for sinusitis treatments, the medication is not absorbed to any great extent by the body because of the size of the medication molecules. What is desired is that the medication lay on the surface and stay there. Because the hooded cavity 20 surrounds the area of the nose where the openings to the sinus cavities are located, the attachment 10 directs the sinusitis medication directly to the only area where it can be effective. For other types of medications which are absorbed into the body, such as pain medications, hormones, etc., the hooded cavity 20 directs the medication spray to the lateral side walls of the nose which contain the most blood vessels. This area is much more efficient in absorbing medication into the blood stream than any other portion of the nose.

Besides providing these advantages, the nasal inhaler of the present invention avoids the disadvantages experienced by the prior art devices. For example, the medication spray is prevented from entering the back of the nose and hence the stomach of the patient. This prevents possible irritation of the patient's stomach. Furthermore, the present invention prevents the medication from contacting the nasal septum, thereby avoiding irritation, ulceration, perforation of the septum, and increased risk of infection. Also, because the medication spray is delivered only to the area to the nose where it is effective, the present invention results in a lower dose of the medication being required for each application. This is particularly important in the case of expensive medications, such as hormones. This is also important in certain medications that produce side effects, as there will be lower side effects if less medication is absorbed into the body from the other surfaces.

It will be appreciated by those skilled in the art after referring to the above description that the attachment 10 of the present invention is merely exemplary of the preferred embodiment. It is preferred that the attachment 10 be formed from a plastic material of the same composition as the nasal inhaler 28. However, other materials may work equally well. It is also contemplated by the present invention that the attachment 10 may be constructed in various sizes in order to accommodate various sized noses. It is also anticipated that the present invention may find use in veterinary applications.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A nasal inhaler having a directed spray pattern, comprising:

a container adapted to hold a quantity of medication and including a container spray outlet; and an attachment coupled to the container spray outlet, the attachment comprising:

a body member having a proximal end, a distal end, a first side and a second side, the body member tapering from the proximal end to the distal end such that the body member is sized and shaped to fit into the nose;

an opening formed into the first side of the body member proximal of the distal end, the opening forming a hooded cavity within the body member; and an axial bore formed in the body member from the proximal end to the cavity;

wherein medication exiting the container spray outlet is directed through the axial bore, into the hooded cavity, and out of the opening such that the medication is directed toward the lateral sidewall of the nose when the body member is inserted into the nose, and the body member substantially prevents the medication from contacting a septum of the nose and a back of a nasal cavity of the nose.

2. The nasal inhaler of claim 1, further comprising:

a flared surface at the proximal end of the body member in addition to said tapering;

wherein the flared surface limits a distance of insertion of the attachment into the nose.

3. The nasal inhaler of claim 1, wherein the body member is substantially frustoconical.

4. The nasal inhaler of claim 1, wherein a distance between a rim of the opening and the second side varies between a proximal end of the rim and a distal end of the rim.

5. The nasal inhaler of claim 4, wherein the distance decreases and then increases between the proximal end of the rim and the distal end of the rim.

6. The nasal inhaler of claim 1, wherein the attachment is detachable from the container.

7. The nasal inhaler of claim 1, wherein the attachment may be rotated with respect to the container.

8. The nasal inhaler of claim 1, wherein the container is further adapted to hold a quantity of propellant.

9. An attachment for connection to a spray outlet of a nasal medication container, the attachment comprising:

a body member having a proximal end, a distal end, a first side and a second side, the body member tapering from the proximal end to the distal end such that the body member is sized and shaped to fit into the nose;

an opening formed into the first side of the body member proximal of the distal end, the opening forming a hooded cavity within the body member; and an axial bore formed in the body member from the proximal end to the cavity;

wherein medication exiting the container spray outlet is directed through the axial bore, into the hooded cavity, and out of the opening such that the medication is directed toward the lateral sidewall of the nose when the body member is inserted into the nose, and the body member substantially prevents the medication from contacting a septum of the nose and a back of a nasal cavity of the nose.

10. The nasal inhaler of claim 9, further comprising:

a flared surface at the proximal end of the body member in addition to said tapering;

wherein the flared surface limits a distance of insertion of the attachment into the nose.

11. The nasal inhaler of claim 9, wherein the body member is substantially frustoconical.

12. The nasal inhaler of claim 9, wherein a distance between a rim of the opening and the second side varies between a proximal end of the rim and a distal end of the rim.

13. The nasal inhaler of claim 12, wherein the distance decreases and then increases between the proximal end of the rim and the distal end of the rim.

14. The nasal inhaler of claim 9, wherein the attachment is detachable from the container.

15. The nasal inhaler of claim 9, wherein the attachment may be rotated with respect to the container.

16. The nasal inhaler of claim 9, wherein the container is further adapted to hold a quantity of propellant.

* * * * *